United States Patent [19]
Swanson et al.

[11] Patent Number: 5,787,880
[45] Date of Patent: Aug. 4, 1998

[54] RESUSCITATION DEVICE

[75] Inventors: Brian E. Swanson; Donald R. Gorsuch, both of Nothboro, Mass.

[73] Assignee: Greenfield Medical Technologies, Inc., Northborough, Mass.

[21] Appl. No.: 604,364

[22] Filed: Feb. 21, 1996

Related U.S. Application Data

[63] Continuation of Ser. No. 150,452, Nov. 10, 1993, abandoned.

[51] Int. Cl.⁶ .................................................. A61M 16/00
[52] U.S. Cl. ........................... 128/202.28; 128/205.13; 128/205.14; 128/205.16
[58] Field of Search ...................... 128/202.28, 202.29, 128/205.13, 205.14, 205.16

[56] References Cited

U.S. PATENT DOCUMENTS

| | | | |
|---|---|---|---|
| 2,907,322 | 10/1959 | Hay | 128/205.16 |
| 3,283,754 | 11/1966 | Goodner | 128/205.14 |
| 3,336,920 | 8/1967 | Thomas | 128/205.16 |
| 3,548,821 | 12/1970 | Gigauri et al. | 128/205.14 |
| 3,918,317 | 11/1975 | Claussen | 128/205.14 |
| 4,067,328 | 1/1978 | Manley | 128/205.14 |
| 4,297,999 | 11/1981 | Kitrell | 128/205.16 |
| 4,349,015 | 9/1982 | Alfremess | 128/205.16 |
| 4,934,360 | 6/1990 | Heilbron et al. | 128/205.16 |
| 5,109,833 | 5/1992 | Frimberger | 128/205.16 |

FOREIGN PATENT DOCUMENTS

| | | | |
|---|---|---|---|
| 1533196 | 7/1968 | France | 128/205.16 |
| 971953 | 10/1964 | United Kingdom | 128/205.16 |

*Primary Examiner*—Aaron J. Lewis
*Attorney, Agent, or Firm*—Rufus M. Franklin

[57] ABSTRACT

A resuscitation device including an air delivery device which has two rigid walls moveable toward and away from each other, is substantially rectangular, but may have rounded corners; a scissor type mechanism is employed to maintain parallelism of the walls; optional adjustment means is provided to adjust the delivered volume from at least 1200 ml. for an adult patient to a lesser amount for children and a still lesser amount for infants; the adjustment device may be coordinated with mens for simultaneously adjusting the maximum delivered pressure to levels appropriate to the adult, child, or infant patient; economy in storage and quantity of devices required is achieved.

8 Claims, 2 Drawing Sheets

RESUSCITATION DEVICE

This is a Continuation of application Ser. No. 08/150,452, filed Nov. 10, 1993, now abandoned.

FIELD OF THE INVENTION

The invention relates to rescue breathing apparatus, in particular to the air delivery system in rescue breathing devices.

BACKGROUND OF THE INVENTION

For several decades, bag-valve mask resuscitators (BVR) have remained quite popular among all levels of rescuers internationally. Such devices consist of an oval resilient self-inflating bag adapted to be manually squeezed to deliver air through a non-rebreathing valve to a mask or endotracheal tube to the patient. As pointed out in the Journal of the American Medical Association, Vol. 268, No. 16, of Oct. 28, 1992, such BVR's, in adults, may provide less than adequate tidal volumes. A single rescuer, it is pointed out, may have difficulty providing a leakproof seal to the face and squeezing the bag adequately with one hand while also maintaining an open airway. Thus such BVR's require at least two well-trained and experienced rescuers working together. Anyone familiar with BVR devices knows that an adult size unit, especially one large enough to provide greater than 1000 ml tidal volume, requires at least a two hand operation to even get close to a full volume delivery. As an alternative, some rescuers have developed methods of squeezing the bag between on hand and some location on the rescuers anatomy such as the thigh or chest. However, even with the use of two hands, or using other methods of squeezing the bag, rarely if ever is an adequate volume delivered to an adult patient via a BVR. Published studies indicate that 800 ml, or less, is most often achieved. The present invention is designed to obviate the difficulties with the prior art BVR's.

SUMMARY OF THE INVENTION

The present invention provides an improved air or air and oxygen delivery system by employing a collapsible bag device having effectively rigid end plates connected by flexible, collapsible walls completing an enclosure so that the end plates can be manually moved together to pump air and/or oxygen to the patient. By the use of generally rectangular end plates of suitable dimensions and suitable spacing of the plates, one handed operation of the device by squeezing the plates together can be effective to deliver suitable amounts of air to the patient. Further, a simple adjustment means is provided to limit the travel; of the plates toward or away from each other so that the volume of delivered air can be adjusted for an adult, an infant, or a child.. For packing, shipping, and storage the devices can be fastened in the collapsed position whereby more efficient use of space is achieved. This, together with the need for only one size of device for infants, children and adults, results in cost savings. This is particularly significant in that, because of fears of contamination these devices generally are disposed of after one use. There is provided means to maintain parallelism of the end plates. The plates may be squeezed together from any of their four sides. Means may be provided for the supply of suplementary oxygen into the air inlet. The shape of the volume defined by the top and bottom rigid walls and the side walls is a rectangular right parallelepiped.

The means for setting the volume delivery may be combined with indication of the proper cadence and depression of the chest for adults, children and infants. The means for setting volume delivery can also be linked to variable relief fixtures to limit maximum pressure deliverable for each size patient.

DETAILED DESCRIPTION

Figure 1:
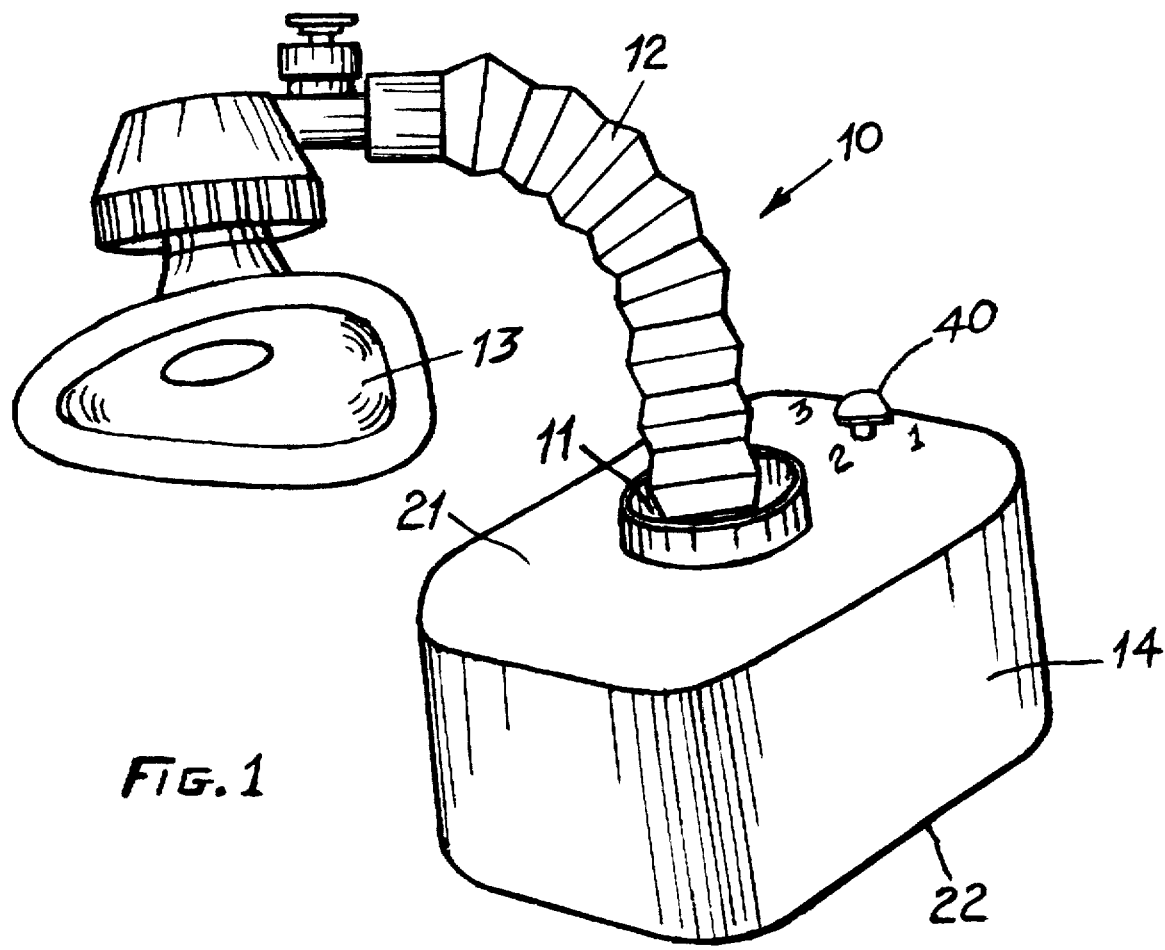
FIG. 1 is a perspective view of the rescue breathing device of the present invention.
Figure 3:
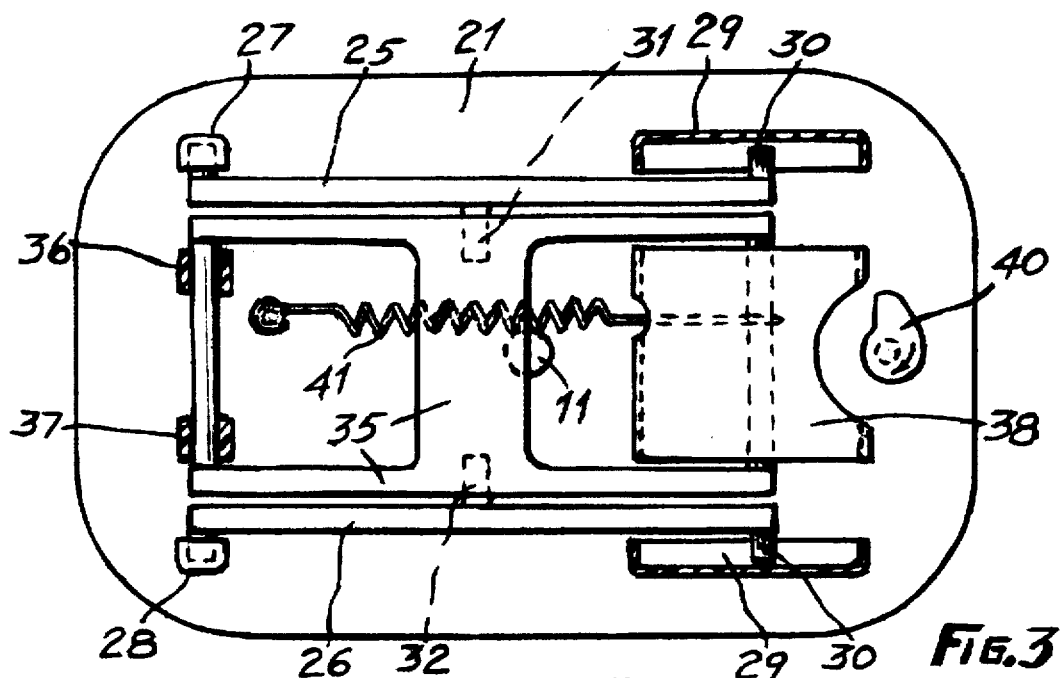
FIG. 3 is a top view of the device of FIG. 2.

FIG. 1 shows a compressible air supply device 10 having an outlet 11 connected to air supply conduit 12 and rescue mask 13 incorporating an industry standard non-rebreathing valve. The device 10 has a gas impermeable covering 14, and is adapted to be squeezed manually from one end or side to deliver air to the mask.

Figure 2:
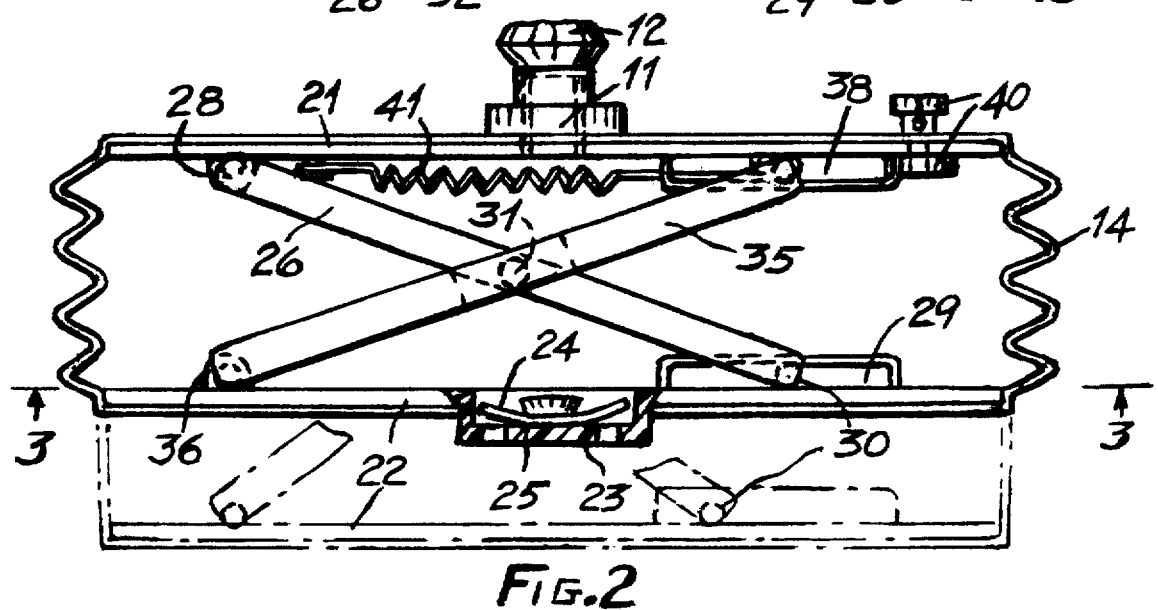
FIG. 2 is a side view of the air pump portion of FIG. 1 with the covering removed.

FIG. 2, a side view of FIG. 1 with the covering 14 removed shows rigid top and bottom walls 21 and 22 with the air outlet 11 in the top wall and an inlet with a check valve 23 having a resilient elastic flapper 24 cooperating with a perforated seat element 25. Upon opening movement of the wall 21 and 22 the member 24 moves away from its seat to allow air to fill the chamber, while when the walls are moved toward each other to deliver air, the element 24 closes against its seat to allow all the air to flow out of outlet 11 to the delivery tube.

To maintain the walls 21 and 22 in a parallel relationship, a scissor type arrangement is provided in the form of outer arms 25 and 26 pivoted respectively in rotary bearings 27 and 28, in the top wall 21 at one end and slidably retained at the other end in cages or slideway 29 in the bottom wall 22. Arms 25 and 26 are provided with studs 31 and 32 which are rotatable in circular bearings in H-shaped member 35, one end of which is pivotally held in bearings 36 and 37 in bottom wall 22, and slidably retained in cage 38 in top wall 21 at the other end. At the end of bottom wall 22, associated with cage 38, is a motion limiting cam device 40 having a manually adjustable control knob on the outside of the wall. Thus the cam can be positioned to limit the closed position of walls 21 and 22 to provide the proper amount of air delivery for an adult, a child, or an infant. A spring 41 is provided attached to one end of the H-shaped member and attached fixedly at the other end to bias the walls 21 and 22 toward the open position. Preferably the spring force is designed to exert its least force as the walls are close to each other and its greatest force when the walls are at maximum separation, for ease in manual operation.

In FIG. 2 the device is shown in an intermediate position of the walls 21 and 22 relative to each other and in phantom lines shows the walls in fully open position.

Figure 5:
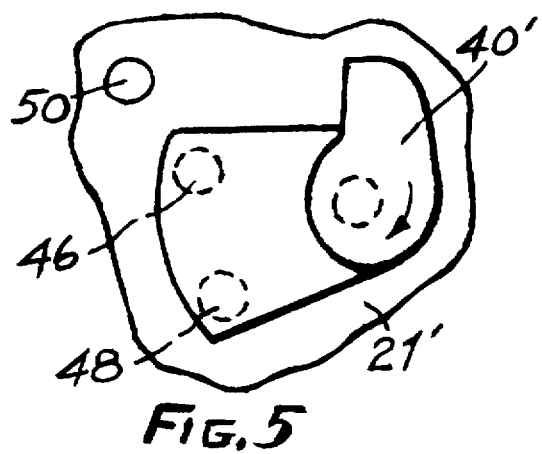
FIG. 5 is a schematic view of a portion of the bottom wall of FIG. 3 showing an optional dual control device.

The partial view in FIG. 5 of the top wall shows a modification of the adjustment cam whereby when the cam is in position to deliver air to an adult it cooperates with a pressure relief valve to adjust its opening for the maximum pressure for an adult, when it is in the child position it adjusts for the maximum pressure for a child, and similarly for an infant. In the modification shown, the relief valve consists of three valves, a low pressure valve 46 for infants, an intermediate pressure valve for children 48, and the highest pressure valve 50, for adults. For an infant all the valves may be uncovered; for the child the infant valve must be covered; for the adult all the valves except the adult must be covered. The position of the cam for the volume appropriate for the infant provides that the infant valve be uncovered. Similarly in the cam position for delivering the correct volume for the child, the infant valve is covered and the child valve is uncovered. Finally, for the adult the full range of motion of the air pump is allowed, and the child and infant valves are covered and thereby closed.

An important advantage of the invention is that the device can be stored in a minimum of space by clamping the sides in the position of minimum volume. Furthermore since one unit is suitable for infants, adults and children, only one size of unit need be stocked thus offering a further economy in space and in cost. This is particularly important in view of the fact that it is the practice to use the units only once because of the danger of infection.

Figure 4:
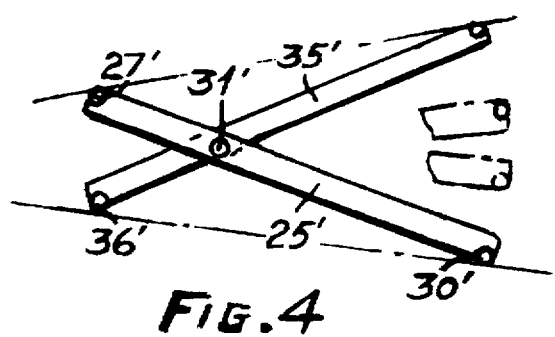
FIG. 4 is a schematic view of a modification of the scissor mechanism of FIGS. 2 and 3.

FIG. 4 is a schematic view of an arrangement of the scissor mechanism whereby the scissor arms are pivoted nearer one end instead of at the center. In this arrangement, pushing the walls together at one the end nearest the pivot causes a greater movement at the far end, while retaining parallelism of the walls in the width direction. This permits easier use of the device by a person with a smaller hand or less fatiguing operation in general. The positions of the H-shaped member 35' and arm 25' in the open position of the air pump are shown in solid lines, while the positions in the close position of the far right ends of these members are shown in dotted phantom lines. In this arrangement, the walls 21 and 22 are retained in a controlled but non-parallel orientation in the long direction, but the width direction elements are retained in a parallel orientation. That is, the ends and all lines parallel to the ends are retained in a parallel relation.

In the modification of FIG. 4 the volume defined by the top and bottom walls is a right rectangular parallelepiped in only one position, when the plates are approxomately fully closed.

The particular dimensions of the elements of the invention are not critical, except that they should be such that a tidal volume of at least 1200 ml is delivered when the device is arranged for use with an adult patient. Typical dimensions giving the device a "footprint" no greater than the BVR devices now in almost universal use, would be 8 inches length by 4.5 inches width (20.3 cms by 11.4 cms). This gives the device an advantage in volume delivery (at least 1200 ml for the adult) as compared to the bag type devices now in use which cannot deliver as large a volume.

Commercial devices are available which give visible light flashes) or audible signals for the timing of chest compressions and ventilation for adults, children, or infants. Such devices may be coupled to the mechanism of the present invention for adjusting the volume of air delivered for an adult, child or infant and triggered by the closure of the of the air delivery plates, such that the cadences are adjusted for adult child or infant in accordance with the American Heart Association standards.

What is claimed is:

1. A resuscitation device including a compressible chamber having two parallel relatively rigid end walls having a length greater than width and flexible side walls defining an internal volume sufficient to deliver an adequate amount of air to an adult, guide means enclosed by said end walls to maintain said end walls in parallel orientation as said end walls are moved toward and away from each other said end walls being resiliently urged apart by said guide means including spring means acting directly on and attached directly to said guide means, an outlet from said internal volume for directing air to a patient and an inlet for admission of oxygen containing gas to said internal volume, and adjustable means for controlling the volume of gas delivered to said outlet by controlling the volume defined by said chamber between maximum and minimum spacing during a compression and expansion cycle.

2. A resuscitation device as in claim 1 in which the force required to squeeze the plates together near the end of a compression cycle is not greater than that required at the beginning of the compression cycle.

3. A resuscitation device as in claim 1 in which said guide means comprise a pivoted slidable scissor type mechanism and said adjustable means is adapted to limit the travel of the slidable scissor type mechanism and has a manually controlled means on the outside of said device having indicia to indicate the volume for a given position of the adjustment device.

4. A resuscitation device as in claim 1 to which an electronic cadence device for timing of chest compressions and ventilations is electrically coupled to and triggered by closure of the resuscitation devices well as being electrically linked to the volume control device such that cadences are adjusted for adult, child, or infant.

5. A resuscitation device as in claim 1 in which the volume delivered to the patient is adjustable and in which the maximum pressure delivered is adjusted in accordance with the volume delivered.

6. A resuscitation device as in claim 1 in which the volume defined by said end walls is a rectangular parallelepiped with rounded corners.

7. A resuscitation device including a compressible chamber having two substantially rectangular, relatively rigid end walls and flexible side walls defining a volume adequate to deliver sufficient tidal volume to an adult, guide means enclosed by said end and side walls to maintain said end walls in parallel orientation in the width direction and a controlled non-parallel relationship in the length direction as said end walls are moved toward and away from each other, said end walls being resiliently urged apart by said guide means, said guide means including a spring means acting on and attached directly to said guide means, an outlet from said internal volume for directing air or oxygen to a patient and an inlet for admission oxygen containing gas to said internal volume.

8. A resuscitation device including a variable volume chamber defined by two spaced relatively rigid end walls and a flexible side wall, said end walls adapted to move toward and away from each other to establish maximum and minimum volumes, guide means to support the movement of said end walls and enclosed in said chamber; resilient means associated with said guide means and end walls consisting of a spring having two ends, one end of which is fixedly attached to an end wall and the other end of which is attached to said guide means to move therewith whereby said end walls are resiliently urged apart, said guide means consisting of two scissor mechanisms spaced parallel to each other and slidably connected at corresponding ends to said end walls and at opposite ends being pivotally connected to said end walls, each of said scissor mechanisms having an outer arm and inner arm, the inner arms being rigidly connected to each other.

* * * * *